(12) United States Patent
Oikawa et al.

(10) Patent No.: US 8,998,814 B2
(45) Date of Patent: Apr. 7, 2015

(54) DIAGNOSTIC ULTRASOUND APPARATUS

(75) Inventors: Katsuya Oikawa, Tokyo (JP); Kenichi Nagae, Yokohama (JP); Yasuhiro Someda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 561 days.

(21) Appl. No.: 12/468,693

(22) Filed: May 19, 2009

(65) Prior Publication Data

US 2009/0299185 A1  Dec. 3, 2009

(30) Foreign Application Priority Data

May 27, 2008  (JP) .................................. 2008-138055
Apr. 13, 2009  (JP) .................................. 2009-097225

(51) Int. Cl.
*A61B 8/00*  (2006.01)
*A61B 8/14*  (2006.01)
(52) U.S. Cl.
CPC .................. *A61B 8/14* (2013.01); *A61B 8/4254* (2013.01)
(58) Field of Classification Search
USPC .................. 600/437, 459, 443, 444, 447, 445
See application file for complete search history.

(56) References Cited

U.S. PATENT DOCUMENTS 4,434,661 A *  3/1984  Miwa et al. ..................... 73/625
5,831,168 A *  11/1998  Shinomura et al. ............. 73/602
7,500,952 B1 *  3/2009  Chiang et al. .................. 600/446
7,828,731 B2 *  11/2010  Baba et al. ...................... 600/437
2006/0219013 A1 *  10/2006  Baba et al. ........................ 73/618
2008/0306371 A1  12/2008  Fukutani et al. ................ 600/407
2009/0275837 A1  11/2009  Shiina et al. .................... 600/459
2010/0043546 A1  2/2010  Kandori et al. .............. 73/504.12

FOREIGN PATENT DOCUMENTS

JP  57-31848  2/1982
JP  59-118139  7/1984
JP  2004-167092 A  6/2004
JP  2005-137581  6/2005

OTHER PUBLICATIONS

English translation of JP 2008-120326 provided by machine translation, filed on May 21, 2008.*

* cited by examiner

*Primary Examiner* — Katherine Fernandez
(74) *Attorney, Agent, or Firm* — Fitzpatrick, Cella, Harper & Scinto

(57) ABSTRACT

A novel diagnostic ultrasound apparatus has a plurality of ultrasound probes 1, delay means pairs 4 and 7 arranged respectively in the plurality of ultrasound probes to electronically delay the timings of transmissions or receptions of ultrasonic waves by the ultrasonic transducers, position/orientation detecting means 10 and delay control signal generating means for generating a delay control signal to control signal delays of the plurality of ultrasonic transducers of the plurality of ultrasound probes, using information acquired from the means 10. The delay control signal is input to the delay means to control the timings of transmission of ultrasonic waves to a target object of examination.

14 Claims, 8 Drawing Sheets

DIAGNOSTIC ULTRASOUND APPARATUS

BACKGROUND OF THE INVENTION

1. Field of the Invention

This invention relates to a diagnostic ultrasound apparatus and a diagnostic imaging apparatus for medical use designed to prepare image data according to an ultrasonic echo signal.

2. Description of the Related Art

Diagnostic ultrasound apparatus for transmitting ultrasonic waves from a plurality of probes, acquiring ultrasonic echo signals and synthesizing a cross-sectional image of living tissue so as to collect many pieces of information more easily than an apparatus using a single probe are known.

Japanese Patent Application Laid-Open No. 2005-137581 discloses a moving image photographing apparatus for acquiring a cross-sectional image of living tissue that has a plurality of ultrasound probes, anchors for rigidly securing them, an acoustic coupling material, a probe switching section, an image data measuring section, an image data synthesizing section and a moving image displaying section.

Each of the plurality of probes transmits an ultrasonic wave and receives an echo signal from living tissue. The probe switching section sequentially switches the echo signals from the plurality of probes and transmits the signals to the image data measuring section and the image data measuring section prepares cross-sectional images of a living body according to the echo signals from the probes. As the probe switching section sequentially switches the echo signals from the probes, the image data measuring section can prepare cross-sectional images, sequentially using image data obtained from different angles. Additionally, the anchors for rigidly securing the plurality of probes are equipped with respective angle sensors for detecting the relative positions of the probes. Thus, the image data synthesizing section can synthetically combine the cross-sectional images sequentially prepared by the image data measuring section by using the relative position information.

In this way, a cross-sectional synthetic image is obtained by shooting a living body from different angles as in the case of sequentially moving a probe. As a cross-sectional synthetic image is obtained by shooting a living body from different angles, the living tissue from which an echo image can hardly be obtained because it is hidden by bone tissue that reflects ultrasonic waves to a large extent can be imaged to make it easy to grasp the inter-tissue positional relationship and collect pieces of information effective for diagnosis.

SUMMARY OF THE INVENTION

However, with a diagnostic ultrasound apparatus described in Japanese Patent Application Laid-Open No. 2005-137581, information relating to the probe positions obtained from the sensors attached to the respective probes is employed only when synthetically combining the images obtained from the probes substantially independently. The probes operate only for focusing from the predetermined respective imaging angles of view. In other words, the shooting operation of each of the probes is substantially invariable regardless of the positional relationship between the living tissue to be imaged and the probe. Therefore, as disclosed in the patent document, even if the plurality of probes are arranged flexibly to accommodate themselves to the profile of the body surface, they are subjected to limitations in terms of directions and angles that should be selected to obtain cross-sectional images that are effective for diagnosing the desired living tissue.

In view of the above-identified problem, it is therefore the object of the present invention to provide a novel diagnostic ultrasound apparatus that is subjected little to such limitations.

According to the present invention, the above object is achieved by providing a diagnostic ultrasound apparatus for transmitting ultrasonic waves to a target object of examination, receiving ultrasonic waves reflected from the target object of examination and preparing image data relating to the target object of examination based on acquired echo signals, the apparatus including: a plurality of ultrasound probes, each being formed to include a plurality of ultrasonic transducers; delay means arranged respectively in the plurality of ultrasound probes to electronically delay the timing of transmission or reception of ultrasonic waves by the ultrasonic transducers; position/orientation detecting means arranged respectively in the plurality of ultrasound probes to detect relative position information and relative angle information of the ultrasound probes; and delay control signal generating means for generating delay control signals for controlling signal delays for the respective ultrasonic transducers, the delay control signal generating means controlling signal delays according to information acquired from the position/orientation detecting means, the timing of transmission of ultrasonic waves from the respective ultrasonic transducers and that of reception of ultrasonic waves reflected from the target object of examination being controlled by inputting a delay control signal to the delay means.

Thus, according to the present invention, the amount of delay of signal transmission/reception for each of the ultrasonic transducers of each of the plurality of ultrasound probes is determined by using relative position information of the plurality of probes. Therefore, the directions of transmission of beams from the plurality of probes and the transmission focusing positions and the reception focusing positions can be appropriately defined. Additionally, an image can be produced by using an addition signal obtained by phasing the signals received from the plurality of ultrasound probes.

Further features of the present invention will become apparent from the following description of exemplary embodiments with reference to the attached drawings.

DESCRIPTION OF THE EMBODIMENTS

Figure 1:
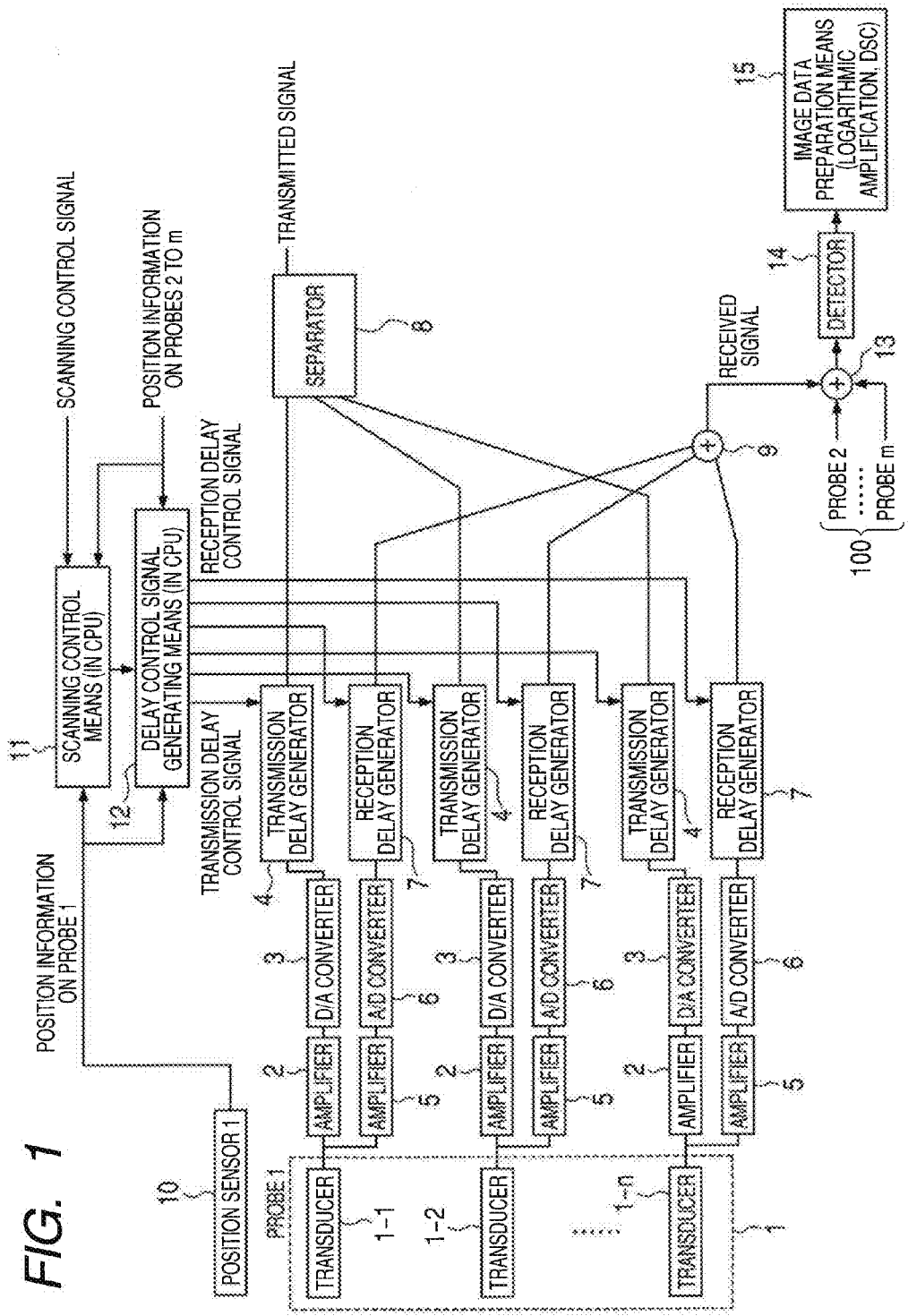
FIG. 1 is a schematic block diagram of an embodiment of diagnostic ultrasound apparatus according to the present invention.

A diagnostic ultrasound apparatus according to the present invention irradiates ultrasonic waves to a target object of examination, receives ultrasonic waves reflected from the target object of examination by means of a plurality of ultrasound probes, each of which is formed to include a plurality of ultrasonic transducers, and prepares image data relating to the target object of examination according to the acquired echo signals.

Thus, the diagnostic ultrasound apparatus according to the present invention has a plurality of ultrasound probes and delay means arranged in each of the plurality of ultrasound probes to electronically delay the timing of transmission or reception of ultrasonic waves by the corresponding one of the ultrasonic transducers. The delay means as used herein refers to a transmission delay generator 4 or a reception delay generator 7 illustrated in FIG. 1.

Additionally, the diagnostic ultrasound apparatus according to the present invention has position/orientation detecting means (position sensor) for detecting relative position information and relative angle information of the plurality of ultrasound probes and delay control signal generating means for generating a delay control signal to control the signal delay for each of the ultrasonic transducers of each of the plurality of ultrasound probes, using the information acquired from the position/orientation detecting means.

The delay control signal generating means controls the signal delay according to the information acquired from the position/orientation detecting means. The information acquired from the position/orientation detecting means is typically relative position information and relative angle information on the plurality of ultrasound probes. The delay control signal generating means controls the signal delay for the plurality of ultrasonic transducers according to the distance from each of the ultrasound probes to a predetermined focusing position. Preferably, a common focusing position is defined for the plurality of ultrasound probes.

The transmission timing of an ultrasonic wave to a target object of examination by each of the ultrasonic transducers and the reception timing of an ultrasonic wave reflected by the target object of examination by each of the ultrasonic transducers can be controlled as a delay control signal is input to the delay means.

(Beam Scanning)

An ultrasonic beam can be scanned so as to shift the direction of transmission of the ultrasonic beam transmitted from each of the ultrasound probes. A delay amount computing means can be utilized to determine the amount of delays for each of the ultrasonic transducers according to the relative position information and the relative angle information on the plurality of ultrasound probes at the time of starting scanning the beam or while the beam is being scanned.

An ultrasonic beam can be scanned so as to shift the direction of reception of the ultrasonic beam received by each of the ultrasound probes. The delay amount computing means can be utilized to determine the amount of delays for each of the ultrasonic transducers according to the relative position information and the relative angle information on the plurality of ultrasound probes at the time of starting scanning the beam or while the beam is being scanned.

(Beam Focusing)

The ultrasonic beam transmitted from each of the ultrasound probes can be subjected to transmission focusing by the delay means. The delay amount computing means can be utilized to determine the amount of delays for each of the ultrasonic transducers according to the relative position information and the relative angle information on the plurality of ultrasound probes at the time of starting scanning the beam or while the beam is being scanned.

The ultrasonic beam reflected from the target object of examination can be subjected to reception focusing by the delay means. The delay amount computing means can be utilized to determine the amount of delays for each of the ultrasonic transducers according to the relative position information and the relative angle information on the plurality of ultrasound probes at the time of starting scanning the beam or while the beam is being scanned.

FIG. 1 is a schematic block diagram of an embodiment of diagnostic ultrasound apparatus according to the present invention. Note, however, that FIG. 1 mainly shows the components that characterize the present invention and some of the components that are popularly known in the technical field of diagnostic ultrasound imaging apparatus for medical use are omitted.

FIG. 1 denotes a probe 1 (the first probe) that is one of the plurality of probes for transmitting and receiving an ultrasonic wave. A number of (n in this instance) ultrasonic transducers 1-1 through 1-*n* are arranged in array. The second and all the subsequent probes are omitted for the purpose of simplicity but they have a configuration same as the first probe. Each of the probes includes components indicated by reference symbols 2 through 7, which will be described in greater detail hereinafter, and a sensor 10, which will also be described hereinafter.

Each of the ultrasonic transducers (1-1 through 1-*n*) of the first probe 1 is connected to a transmission amplifier 2, a reception amplifier 5, a D/A converter 3, an A/D converter 6, a transmission delay generator 4 and a reception delay generator 7. The transmission delay generator 4 is connected to a separator 8, while the reception delay generator 7 is connected to an adder 9.

While the transmission amplifier 2, the reception amplifier 5, the D/A converter 3, the A/D converter 6, the transmission delay generator 4 and the reception delay generator 7 are provided separately for reception and transmission in FIG. 1, the entire apparatus can be simplified by adopting a sharing arrangement for transmission and reception. Such an arrangement provides an advantage of reducing the number of parts to make the entire apparatus compact and reduce the cost. However, the arrangement of FIG. 1 enables to select, for example, an amplifier that can produce a high voltage for transmission and an amplifier that can produce a low noise level for reception. In this way, components having different characteristics can be selectively operated depending on the required function(s).

The transmission delay generator 4 and the reception delay generator 7 are for producing a time delay to a digital time series signal respectively according to a reception delay control signal and a transmission delay control signal. Each of them can be formed by using a known digital delay circuit. Of course, a delay can be produced by storing an input digital time series signal in a memory and reading the signal out at a timing that corresponds to the amount of delay to be produced. Additionally, a transmission delay control signal and a reception delay control signal can be made to include signal amplitude information. If such is the case, the transmission delay generator 4 and the reception delay generator 7 may be made to have an amplitude boosting function of digitally multiplying an input signal in addition to a digital delay circuit. Such an arrangement enables to execute an apodization process, which will be described in greater detail hereinafter. In the case of transmission, for instance, an apodization process is a process of using different amplitudes for the transmission signals of a plurality of oscillators contained in a single probe. In the case of reception, an apodization process is a process of using different amplitudes for the reception signals.

Each of the probes is annexed by a position sensor.

While the first position sensor 10 that is annexed to the first probe 1 is illustrated in FIG. 1, each of the remaining probes (not illustrated) is also annexed by a similar position sensor. The first position sensor 10 detects the position and the relative angle of the first probe 1 and the azimuth angle of the ultrasonic transducer array. The position, the relative angle and the azimuth angle can be detected by using a magnetic sensor, an optical sensor and a rotary encoder in combination. Particularly, they can be detected by a linear sensor and the rotary encoder arranged at the holder holding a probe as will be described hereinafter.

While the first position sensor 10 is a position/angle composite sensor in this sense, it is simply referred to as position sensor in this specification for the purpose of simplicity.

As described above, each of the remaining probes other than the first probe is also provided with a similar position sensor to be able to detect the position and relative angle of each of the remaining probe, and the azimuth angle of the ultrasonic transducer array. The expression of position as used herein may refer to the relative positions of a plurality of probes or the relative position of each probe relative to some reference position. The expression of relative angle may refer to the angle formed by the directions of two probes or the angle that each probe forms with a reference direction. The azimuth angle of an ultrasonic transducer array may be the angle relative to the probe to which it belongs (the rotary angle relative to the direction of a transmitted or received beam that operates as axis).

The position, and the relative angle of the first probe 1, and the azimuth angle of the ultrasonic transducer array detected by the first position sensor 10 are input to a scanning control means 11 and a delay control signal generating means 12.

The outputs from the second and subsequent position sensors that are annexed respectively to the second and subsequent probes and detect the position, the relative angle and the azimuth angle of the ultrasonic transducer array of the respective probes are also input to the scanning control means 11 and the delay control signal generating means 12.

While the scanning control means 11 and the delay control signal generating means 12 can be formed by using electronic circuits, the processing methods thereof may be programmed in the CPU. While the scanning control means 11 and the delay control signal generating means 12 are described above as separate means, they may be realized by programming separate processing methods for them in the CPU.

(Data Preparation Sequence)

Now, the living tissue cross-sectional video data preparation sequence of this embodiment will be described below.

Normally, cross-sectional video data are formed by a plurality of time series data of cross-sectional images. These cross-sectional images are referred to as frame images. In this embodiment, image data of a cross-sectional image are prepared also on a frame image by frame image basis to produce cross-sectional video data that are time series data in order to display a cross-sectional video. The process of preparing a frame image data is referred to as a frame process.

In the frame process, firstly a cross section plane that transversally crosses the target living tissue is selected and is divided by a plurality of image scanning lines to prepare each cross-sectional image data (frame image data).

Then, the direction of the ultrasonic beam transmitted from each probe and the direction of the received ultrasonic beam are scanned in order to obtain data on each image scanning line (to be referred to respectively as "transmitted beam direction" and "received beam direction" hereinafter).

The transmitted ultrasonic beam is focused in order to effectively irradiate a target. The transmission focusing is for converging the transmitted ultrasonic wave to one or more than one points (transmission focusing point(s)) in the transmitted beam direction. The transmitted ultrasonic wave is converged by generating a delay to the ultrasonic pulse generated from each of the ultrasonic transducers of each probe.

At the time of receiving ultrasonic echoes, a delay is generated to the echo signal received by each of the ultrasonic transducers of each probe so that the echo from each of the points in the received beam direction is converged before being received for the transmitted ultrasonic pulse propagating along the converged transmitted beam. Thus, the received ultrasonic beam is subjected to reception focusing in this way. A plurality of points for reception focusing (reception focusing points) may be defined corresponding to the propagation of ultrasonic wave at the time of reception.

An image scanning line data is prepared from the echo signal received as a result of defining the transmitted beam direction, the timing of transmitting a pulse and the received beam direction.

For example, the direction of the image scanning line is preferably made to agree with the transmitted beam direction of any of the plurality of ultrasound probes. In such a case, the reception focusing points of the plurality of probes are moved in the transmitted beam direction while the focusing points of each probe are made to agree with each other according to the timing of propagation of the ultrasonic pulse transmitted from the probe. With this arrangement, ultrasonic echoes from the living tissue of the transmitted ultrasonic pulse can be received as time series signals simultaneously by the plurality of probes.

In this way, the ultrasonic echo signals from the points on the image scanning line are prepared in each of the probes as time series signals. Then, a similar operation is conducted sequentially for adjacent image scanning lines to obtain a plurality of rows of time series signals that correspond to the image scanning lines of the cross section plane. Thus, as a result, a cross-sectional image is obtained from the ultrasonic echoes. A synthetic beam formed by combining beams transmitted from a plurality of probes can be used as transmitted beam. Then, ultrasonic echoes can be received as time series signals by the probes as the reception focusing points of each probe are moved along the direction of the synthetic beam, which is the direction of image scanning lines. With this arrangement, the ultrasonic echo signals from various points of living tissue get to the ultrasound probes substantially simultaneously.

In a characteristic application of the present invention, the positions and the orientation angles of the plurality of probes and the azimuth angles of the ultrasonic transducer arrays are detected and a delay is generated for the reception signal of each of the ultrasonic transducers of each of the probes according to the detected information. In this way, the echo signals from a same point of living tissue are synchronized on the echo time series signals from each of the ultrasonic transducers and time series echo signals are prepared by means of phasing addition of the signals from each probe to produce a single cross-sectional image. An effect of synthetically combining the apertures of the ultrasonic transducer arrays of the probes by means of phasing addition of the echo signals from the plurality of ultrasound probes can be obtained. Generally, the resolution is improved in the transversal direction as the apertures of the ultrasonic transducer arrays increase. For example, in the technical field of electric wave radar, the resolution can be improved by means of phasing addition of the outputs of a plurality of antenna elements having limited apertures. Thus, a diagnostic ultrasound apparatus having a plurality of probes can be made to operate for aperture synthesis to improve the resolution of the ultrasonic echo cross-sectional image the apparatus produces.

The present invention is also applicable to preparation of a 2D or 3D image by preparing cross-sectional image data by means of each of a plurality of probes and synthetically combining the image data instead of preparing a single cross-sectional image data by means of phasing addition of reception signals from a plurality of probes as described above. In other words, alignment is conventionally important for registration of image data when forming a 2D or 3D image on the basis of the cross-sectional image data prepared by each of the probes. Then, the limit of accuracy of the alignment on the basis of the image data is defined by the pixel unit of the image data. However, when scanning and focusing are conducted at the time of reception as described above for the embodiment of the present invention, the time series signals from each of the probes that correspond to the above-described image scanning are not positionally significantly displaced on the corresponding signals from the echo sources of living tissue because the time series signals are synchronized with the corresponding signals.

Additionally, the echo RF signals before the detection have a carrier frequency that is an ultrasonic frequency. Therefore, the relative displacements of signals among the echo time series signals from different probes can be detected with a level of accuracy lower than ultrasonic wavelengths by using a known phase detection technique such as phase measurement by quadrature detection or cross correlation detection. Then, the image data among the probes can be synthetically combined with a positional accuracy of about the operating ultrasonic wavelength by means as a result of such detection. Generally, the operating ultrasonic wavelength is smaller than the pixel size of image data and hence the accuracy of image data synthesis is improved.

A plurality of ultrasound probes may be divided into several groups and an image data may be prepared by means of phasing addition of the echo time series signals from each of the different groups of ultrasound probes. Then, the image data of the groups may be synthetically combined by alignment in a manner as described above for echo time series signals.

The image scanning lines may be formed by the transmitted beams from a plurality of probes.

Generally, a transmitted ultrasonic wave is attenuated because it is absorbed and scattered by living tissue. Particularly, it is believed that a high frequency ultrasonic wave with a frequency not less than about 10 MHz that can be absorbed to a large extent can obtain a cross-sectional image of only a surface layer or a shallow part from the surface layer, although such an ultrasonic wave provides a high resolution in the thickness direction because of a short wavelength. On the other hand, the transmitted beams from a plurality of probes that are subjected to transmission focusing to a same point in a deep part of living tissue give rise to interference of ultrasonic waves when they are made to intersect the point to form a transversally long high sound pressure region at and near the point as a function of the crossing angles of the beams.

The arrival timings of transmitted ultrasonic pulses and the phases of transmitted pulse waveforms can be made to agree with each other by detecting the position and the orientation angle of each of the probes and the azimuth angle of the ultrasonic transducer array and generating a delay to the transmitted signal of each of the ultrasonic transducers of each of the probes according to what are detected. Each of the probes are made to transmit an ultrasonic pulse so as to be in phase with other transmitted ultrasonic pulses in order to synthetically combine the ultrasonic waves from the probes by interferences in the crossing region of the transmitted beams. Then, as a result, a high sound pressure region can be formed efficiently. It will be appreciated that transmission of waves so as to make them in phase with each other at a focusing point corresponds to synthetic combination of ultrasonic array apertures of probes to increase the effective aperture. It is well known that a fine beam can be focused when the aperture is large at the time of transmission as in the case of reception so that the high sound pressure region of the crossing region of transmitted beams is narrowed to enable to effectively raise the sound pressure.

Such transmission focusing of a diagnostic ultrasound apparatus provides the following advantages. When high output power ultrasonic transducers are employed to obtain a biometric picture of a deep part of living tissue and ultrasonic waves are transmitted from the body surface, ultrasonic waves passes the body with a high intensity at and near the surface layer of the body to consequently damage the tissue. The ultrasonic transmission method according to the present invention as described above provides an advantage of hardly damaging tissues of the surface layer because the method effectively exploits focusing at a deep part of the body by means of an ultrasonic transducer array having a large effective aperture. Particularly, since the above-described ultrasonic transmission method synthetically combines apertures of a plurality of probes for use, it is effective in a case, for example, of heart that is partly covered by bone and for which a sufficiently large aperture to the body surface cannot be formed in a region where ultrasonic waves can reach. More specifically, for example, transmitted ultrasonic waves can be converged effectively and a high luminance image can be obtained from a deep part of living tissue by arranging the apertures of a plurality of probes at a part devoid of bone and synthetically combining the apertures.

Figure 2:
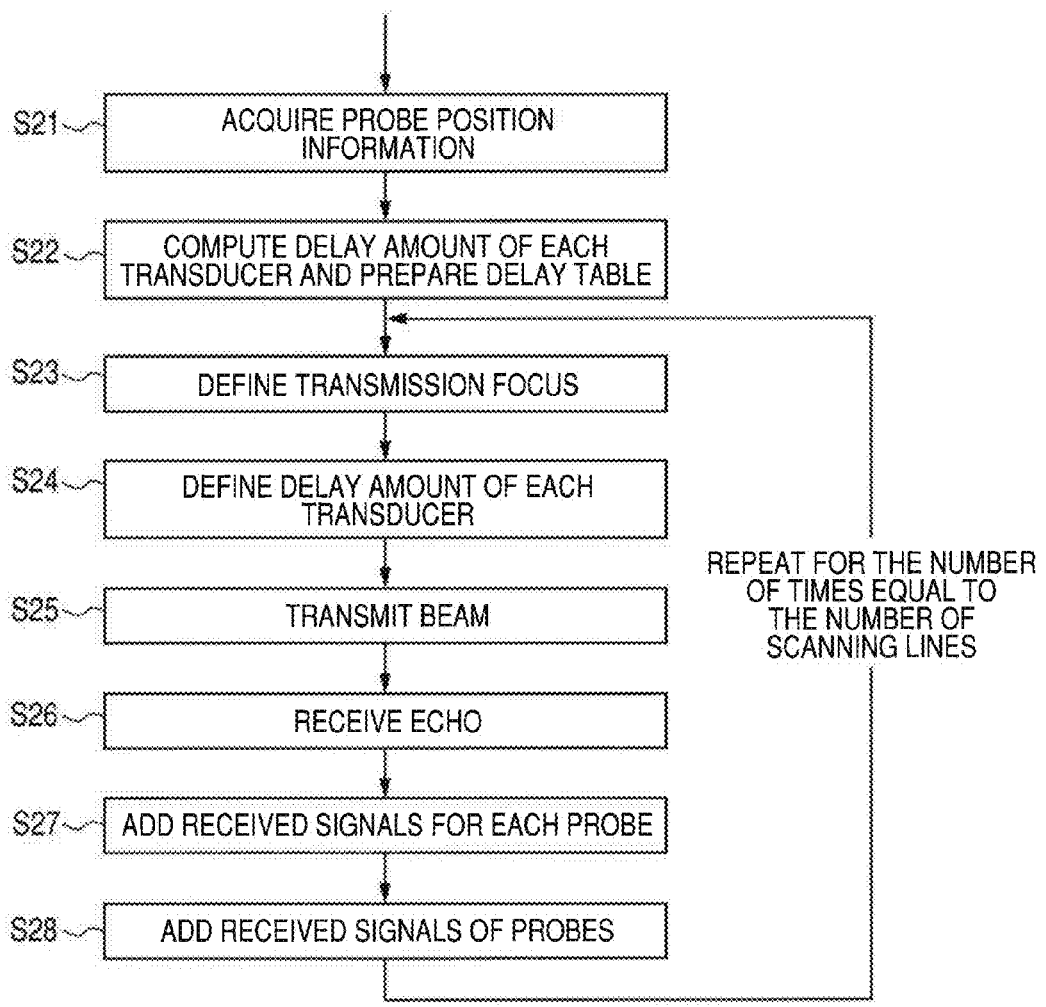
FIG. 2 is a process flowchart illustrating the operation of the embodiment of FIG. 1.

FIG. 2 is an exemplary process flowchart illustrating the operation of the embodiment of the present invention.

What is characteristic here is that the results of computation of the delay amount computing means are written in a delay amount table before starting a beam scanning operation by the ultrasound probes and each of the plurality of ultrasonic transducers of each of the ultrasound probes is controlled for signal delay according to the delay amount table during the beam scanning operation. Now, the process flow will be described below in detail.

In this instance, the position of each of the probes is measured by the position sensor 10 of the probe for each frame process of preparing a frame image that is a time series cross-sectional image. Then, the delay amount of each of the transmission delay generators 4 and/or that of the corresponding one of the reception delay generators 7 that are connected to each of the ultrasonic transducer array of each of the probes is computed by the delay amount computing means, using the information obtained by the measurement. The delay amount computing means is formed by an electric circuit in the scanning control means 11 or the delay control signal generating means 12 or as a program on the CPU. The delay control signal generating means 12 transmits a delay control signal to each of the transmission delay generators 4 and the corresponding one of the reception delay generators 7 of each probe according to the timing of transmission and reception on the basis of the set of delay amounts of the transmission delay generator 4 and/or the reception delay generator 7 computed by the delay amount computing means. Transmitted beams and received beams are formed in this way.

To execute these processes, firstly, the position sensor 10 detects probe position information including the position and the orientation angle of each of the ultrasound probes and the azimuth angle of each of the ultrasonic transducer arrays (S21).

The delay amount computing means computes the delay amount for each of the transducers of each of the probes according to the position information of the probes in response to the scanning control signal applied to the scanning control means 11 and prepares a delay amount table for each of the transducers of each of the probes (S22).

The scanning control signal includes information on the method of scanning the transmitted beam and the received beam selected from the above-described various scanning methods. More specifically, the scanning control signal includes information on the cross section plane to be desirably obtained, the direction of image scanning lines and the transmission focusing point and the reception focusing point on each image scanning line. A plurality of transmission focusing points and a plurality of reception focusing points may be selected depending on the scanning method and timing information for defining each focusing point may be included in the signal.

The delay amount table may describe the delay amount for each of the transducers for each of the scanning angles, of each of the probes and, if there are a plurality of focusing points, for the timing of selecting each of the focusing points.

The flowchart of FIG. 2 is characterized in that information is collected from the position sensor 10 for each frame process before scanning all the image scanning lines of the cross section plane to be desirably obtained.

Accordingly, a delay amount table may be prepared for a single scanning of the image scanning lines of the cross section plane before the scanning. With such an arrangement, the increase of the scanning processing time that arises because of the arithmetic operations performed for the delay amount table during the scanning can be avoided. Then, as a result, the effective scanning time can be reduced to minimize the distortion of the image produced when scanning the cross section plane due to the movement of the body that is produced by heart beats or the like. Additionally, since the arithmetic operations for computing the delay time are performed only once before actually scanning the cross section plane, the overall frame rate can be prevented from rising.

Position information of each of the probes is acquired for each frame process and the delay amount is computed according to the acquired information in this embodiment. Therefore, if the relative position of a probe fluctuates between frame processes, the delay amount of the transmission delay generator 4 and/or the reception delay generator 7 can be controlled to cope with the fluctuations.

Particularly, beam scanning operations and beam focusing operations are conducted for transmission and reception by using a computed delay time according to the present invention. Therefore, if compared with the prior art of synthetically combining frame images independently by using each of the probes, fluctuations of the probe position affect not only the accuracy of synthesizing a cross-sectional image from frame images but also the resolution of the beam for forming an image and the accuracy of the direction of scanning lines. Therefore, fluctuations of the probe position are desirably reflected to the delay amount control with time intervals at least less than the time intervals of forming frame images.

In this embodiment, the delay amount is updated at the time of staring a frame process. Therefore, the delay amount control is made to accommodate any fluctuations of the probe position at time intervals not smaller than the time intervals of frame processes and the increase in the volume of the processing operation is suppressed to avoid any significant increase of time interval between frame processes. Therefore, this embodiment operates satisfactorily.

Now, the method of computing the delay amount $\tau_j^{(i)}$ of ultrasonic transducer j of probe i will be described below. The delay amount $\tau_j^{(i)}$ of ultrasonic transducer j of probe i is determined by the formula illustrated below:

$$\tau_j^{(i)} = \frac{|\vec{R}_f - (\vec{R}_i + \vec{r}_j)| - |\vec{R}_f - \vec{R}_0|}{c} \quad \text{(formula 1)}$$

where i and j respectively represent the probe and the ultrasonic transducer in the probe and $R_f$ and $R_i$ are respectively the three-dimensional position vector indicating the position of each transmission or reception focusing point and the three-dimensional position vector indicating the reference position of probe i, which may typically be the center position of the ultrasonic transducer array of the probe while $r_j$ is the three-dimensional position vector indicating the relative position of the ultrasonic transducer j relative to the reference position of the probe and $R_0$ is the three-dimensional position vector indicating the position of the reference origin of the coordinate system.

For the purpose of simplicity, $R_0$ may be made to be the three-dimensional position vector indicating the reference position of one of the plurality of probes. Note, however, that the delay time amount can be a negative value depending on the selection of $R_0$. If such is the case, all the delay time can be turned to become positive by adding a constant base delay amount for all the ultrasonic oscillators to all the probes.

$R_i$ can be determined according to the probe position information from the position sensor. The relative position of each ultrasonic transducer in a probe is fixed in the ultrasonic transducer array and $r_j$ can be computationally determined by using the positions of all the ultrasonic transducers in the probe and the relative orientation of the probe that can be obtained from the information on the orientation angle of each of the probes and the azimuth angle of the ultrasonic transducer array of the probe. $R_f$ is given as the desired transmission and reception focusing positions within the scanning control signal for the image scanning lines and the transmission and reception timings. Particularly, information for dynamically modifying the transmission and reception focusing while acquiring echo reception data of image scanning lines can be given to the scanning control means 11 at the time of starting a frame process by changing the value of $R_f$ according to transmission and reception timings and collectively giving the obtained values as a scanning control signal.

Now, the delay amount for each ultrasonic transducer of probes will be described in greater detail by referring to FIGS. 8A and 8B. Take two probes 1a and 1b here to make the description easy to understand. The center of the probe 1a is selected as reference for the coordinates of each position. Then, the reference position $R_0$ of the coordinate system is indicated by a nil vector. The center of the probe 1a also operates as reference for the coordinates of the position of a focusing point.

Figure 8A:
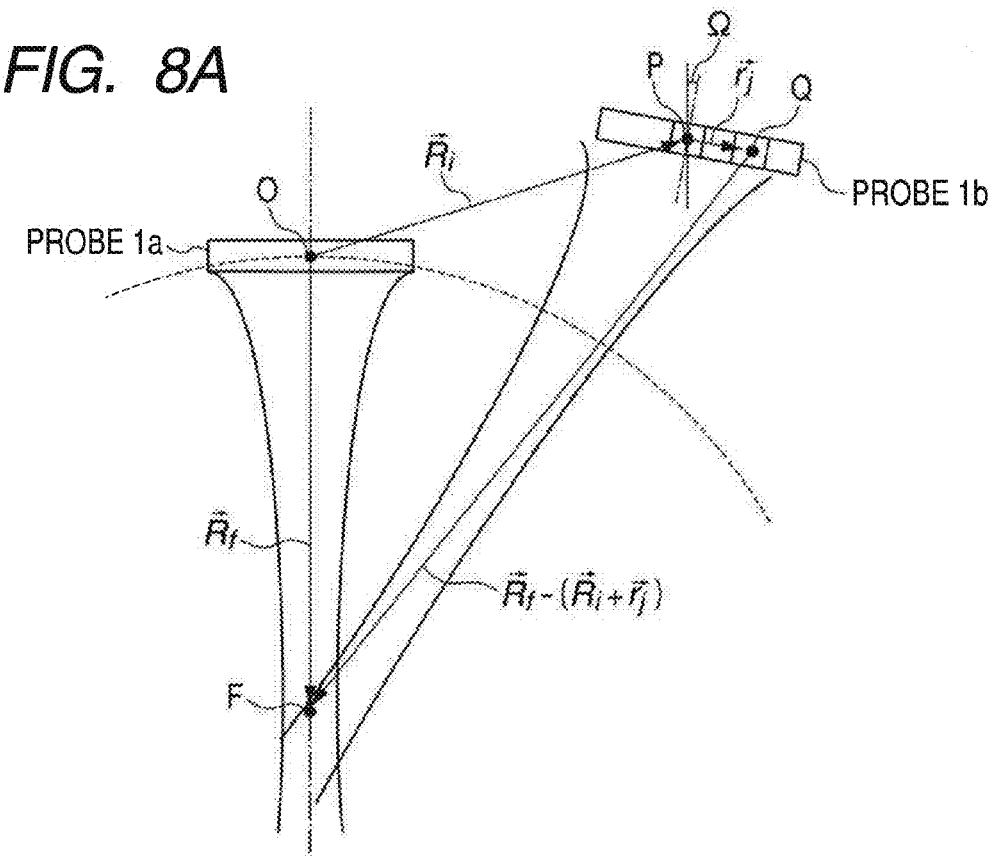
FIGS. 8A and 8B are schematic illustrations of the operation of the embodiment of FIG. 1.

FIG. 8A is a schematic illustration of the positional relationship of the two probes, the ultrasonic transducers on the probes and the focusing point. FIG. 8B is a schematic illustration of the relationship of the relative directions of the ultrasonic transducer arrays on the two probes.

Firstly, probe position information (relative position information and relative angle information) will be described by referring to FIG. 8B. The relative position of each of the ultrasonic transducers of each probe is determined by the position of the ultrasonic transducer in the ultrasonic transducer array. In FIG. 8B, 101a denotes the ultrasonic transducer array in probe 1a and 101b denotes the ultrasonic transducer array in probe 1b. In FIG. 8B, the ultrasonic transducers are illustrated as 2D array type.

The position of a transducer on an ultrasonic transducer array of a probe can be expressed by a three-dimensional vector, using a three-dimensional coordinate system fixed to the probe. In FIG. 8B, x, y and z are employed for the three-dimensional coordinate system fixed to the probe 1a and the three-dimensional position vector of each of the ultrasonic transducers relative to the reference position O of the probe 1a is expressed by $\rho j^{(1a)}$. Similarly, x', y' and z' are employed for the three-dimensional coordinate system fixed to the probe 1b and the three-dimensional position vector of each of the ultrasonic transducers relative to the reference position O' of the probe 1b is expressed by $\rho j^{(1b)}$.

Figure 8B:
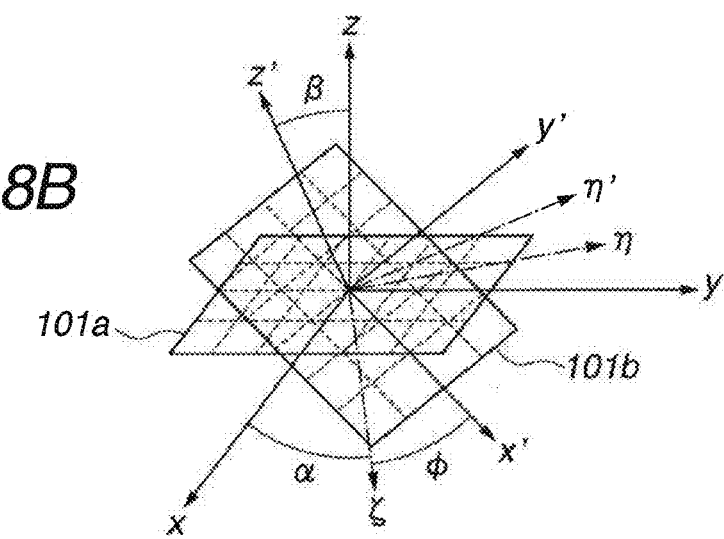

In FIG. 8B, the reference position O of the probe 1a and the reference position O' of the probe 1b are laid one on the other in order to show the relative direction of each of the ultrasonic transducer arrays. Generally, a 2D array type ultrasonic transducer array is found substantially in a plane so that the planes formed by the ultrasonic transducer arrays are expressed by x-y and x'-y' and the 2D arrays are preferably but not necessarily arranged in the planes defined by the respective combinations of the x-axis and the y-axis and x'-axis and the y'-axis. Furthermore, position of each of the ultrasonic transducers on the ultrasonic transducer array of a probe may be shifted in the thickness direction of the ultrasonic transducer array as in the case of convex type ultrasonic transducers so that $\rho j^{(1a)}$ and $\rho j^{(1b)}$ may be expressed by three-dimensional vectors. In this embodiment, the z-direction and the z'-direction are respectively normal directions, or the directions of the probes of the ultrasonic transducer arrays of the probes 1a and 1b.

The relative direction of each of the ultrasonic transducer arrays on the two probes can be specified by using the relative orientation angle ($\alpha$, $\beta$) and the relative azimuth angle ø of the probe. The relative orientation angle ($\alpha$, $\beta$) can be defined in a manner as described below due to the rotational relationship of the coordinate systems x-y-z and x'-y'-z'.

Firstly, the former coordinate system is rotated around the z-axis (counterclockwise) by angle $\alpha$. As a result of the rotation, the x-axis is turned to $\xi$-axis and the y-axis is turned to $\eta$-axis. Subsequently, it is rotated around the $\xi$-axis by angle $\beta$ so that the z-axis is turned to the z'-axis and the $\eta$-axis is turned to $\eta'$-axis. The relative orientation angle of the entire probe 1a and the entire probe 1b is determined by the two angles of $\alpha$ and $\beta$. Thereafter, the $\xi$-axis and the $\eta'$-axis respectively lie on the x'-axis and the y'-axis when the $\xi$-axis and the $\eta'$-axis are turned around the z'-axis by the relative azimuth angle ø.

The method that can be used for measuring the relative orientation angle ($\alpha$, $\beta$) and the relative azimuth angle ø is not limited to the above defined one so long it can determine the difference between the relative orientations of the probes and the direction of each of the ultrasonic transducers relative to the related probe. However, the method to be used is preferably designed to measure the relative orientation angle of the probes and the relative azimuth angle by synthesizing the rotation relative to each probe. Further, the method to be used is preferably designed to measure the relative orientation angle ($\alpha$, $\beta$) and the relative azimuth angle ø of the probe as synthesis of the rotation of the probe relative to the probe holding part by using the position sensor annexed to the probe.

The above-described method can measure the relative to orientation angle ($\alpha$, $\beta$) and the relative azimuth angle ø by measuring angles relating to the z-axis, the z'-axis and the $\xi$-axis. Note that the z'-axis is an axis obtained by turning the z-axis and the $\xi$-axis is obtained by turning the x-axis. Therefore, it is only necessary to measure the angles of rotation of the two axes at the probe holding part so that the design of the rotation measuring part of the position sensor annexed to each probe can be simplified. Since this method requires measuring rotations in the order thereof, the relative orientation angle ($\alpha$, $\beta$) and the relative azimuth angle ø may be measured by an ordinary method of measuring rotations around the three axes. In the following description, the relative orientation angle ($\alpha$, $\beta$) and the relative azimuth angle ø measured by the above-described method will be employed. However, the present invention is by no means limited thereto and rotations around the three axes may be measured by an ordinary method for converting a coordinate system.

Now, the method of computing the delay amount will be described by referring to FIG. 8A.

As a probe reference position is adopted in a manner as described above, the delay amount can be determined for each of the ultrasonic transducers in the probe 1a as in the case of a single probe. More specifically, the delay amount of the j-th ultrasonic transducer of the probe 1a can be computed by means of the formula illustrated below, assuming nil vectors for Ri and R0.

$$\tau_j^{(1a)} = \frac{|\vec{R}_f - \vec{r}_j^{(1a)}| - |\vec{R}_f|}{c} \quad \text{(formula 2)}$$

As clear from FIG. 8A, the delay amount is based on the distance from the reference point O of the probe 1a to the focus point F.

In the above formula, $rj^{(1a)}$ is the three-dimensional position vector that indicates the position of the j-th ultrasonic transducer of the probe 1a. This can be computed as $$\begin{pmatrix} [\vec{r}_j^{(1a)}]_x \\ [\vec{r}_j^{(1a)}]_y \\ [\vec{r}_j^{(1a)}]_z \end{pmatrix} = \begin{pmatrix} 1 & 0 & 0 \\ 0 & 1 & 0 \\ 0 & 0 & 1 \end{pmatrix} \begin{pmatrix} [\vec{\rho}_j^{(1a)}]_x \\ [\vec{\rho}_j^{(1a)}]_y \\ [\vec{\rho}_j^{(1a)}]_z \end{pmatrix} \quad \text{(formula 3)}$$

using the three-dimensional position vector $\rho j^{(1a)}$ of the transducer in the coordinate system fixed to the probe 1a. In the above formula, [ ]x, [ ]y and [ ]z are respectively the x-component, the y-component and the z-component of the three-dimensional vector.

On the other hand, the delay amount of an ultrasonic transducer in the probe 1b is computed by using the probe position information including the position, the orientation angle and the azimuth angle that are determined by the position sensor (not illustrated) annexed to the probe 1b. In FIG. 8A, the center of the probe 1a, the center of the probe 1b and the focus point are indicated respectively by O, P and F. The relative position OP of the probe 1a and the probe 1b is computed from the probe position information of the position sensors annexed to the respective probes. When the above-described positional reference is selected, the relative position OP corresponds to the three-dimensional vector Ri of the formula 1. Similarly, the relative orientation angle $\theta$ of the two probes and the relative azimuth angle ø can be computed from the orientation angles of the probes and the azimuth angle obtained from the position sensors annexed to the respective probes 1a and 1b. In FIG. 8A, the relative orientation angle θ and the relative azimuth angle ø are collectively indicated by Ω because they should be illustrated on a plane. The relative orientation angle θ and the relative azimuth angle ø illustrate the difference in the relative direction between the arrangement of ultrasonic transducers of the probe 1a and the arrangement of ultrasonic transducers of the probe 1b. Thus, the position vector $rj^{(1b)}$ of the j-th ultrasonic transducer on the probe 1b can be computed by using the formula illustrated below.

$$\begin{pmatrix} [\vec{r}_j^{(1b)}]_x \\ [\vec{r}_j^{(1b)}]_y \\ [\vec{r}_j^{(1b)}]_z \end{pmatrix} = \qquad \text{(formula 4)}$$

$$\begin{pmatrix} \cos\alpha\cos\phi - \sin\alpha\cos\beta\sin\phi & -\cos\alpha\sin\phi - \sin\alpha\cos\beta\sin\phi & \sin\alpha\sin\beta \\ \sin\alpha\cos\phi + \cos\alpha\cos\beta\sin\phi & -\sin\alpha\sin\phi + \cos\alpha\cos\beta\sin\phi & -\cos\alpha\sin\beta \\ \sin\beta\sin\phi & \sin\beta\cos\phi & \cos\beta \end{pmatrix}$$

$$\begin{pmatrix} [\vec{\rho}_j^{(1b)}]_x \\ [\vec{\rho}_j^{(1b)}]_y \\ [\vec{\rho}_j^{(1b)}]_z \end{pmatrix}$$

The three-dimensional position vector $\rho j^{(1b)}$ is a position vector indicating the position of the transducer in terms of the coordinate system fixed to the probe 1b. In the above formula, [ ]x, [ ]y and [ ]z are respectively the x-component, the y-component and the z-component of the three-dimensional vector. Furthermore, the delay amount to be given to the j-th ultrasonic transducer on the probe 1b is computed by the formula illustrated below.

$$\tau_j^{(1b)} = \frac{|\vec{R}_f - (\vec{R}_i + \vec{r}_j^{(1b)})| - |\vec{R}_f|}{c} \qquad \text{(formula 5)}$$

As seen from FIG. 8A, the delay amount is also expressed by using the distance from the reference point O of the probe 1a to the focus point F as reference. Thus, a delay amount synchronized with the probe 1a can be computed for the probe 1b that is different from the probe 1a.

While the above description is given by using position vectors defined by referring to the center of the probe 1a, three-dimensional position vectors $R_i$ and $R_f$ can be defined by observing the corresponding positions from a same reference point. Then, the reference of delay can be modified by using a three-dimensional position vector $R_O$ defined by observing a corresponding position from the same reference point.

While the above description is given by using two probes, the delay amount of each ultrasonic transducer can be computed by means of the same method and the formula 1, if three or more probes are used.

Thus, the delay amount of each of the ultrasonic transducers of each of the probes can be computed for a frame process by acquiring probe position information including the position and the orientation angle of each probe and the azimuth angle of the ultrasonic transducer array thereof by means of the position sensor 10 at the beginning of the frame process. In this way, the delay amount to the transmission delay generator 4 and/or the reception delay generator 7 for each of the ultrasonic transducers of each probe for the transmission and reception timings can be described in the delay table by means of the delay amount computing means.

The initial transmission focus is defined according to the scanning control signal (S23). The delay control signal generating means 12 transmits a transmission delay control signal to the transmission delay generator 4 of each of the ultrasonic transducers according to the delay amount table and the delay amount is defined for each of the ultrasonic transducers in the transmission delay generator 4 (S24).

At the same time, the delay control signal generating means 12 may transmit information on the delay amount for reception at the first timing as reception delay control signal to the reception delay generator 7 of each of the ultrasonic transducers according to the delay amount table and the reception delay generator 7 may define it as the initial reception delay. After defining the delay amount, the apparatus moves to an operation of transmitting an ultrasonic pulse.

The transmission pulse signal generated by a transmission signal generator (not illustrated) is broken down for the individual ultrasonic transducers by the separator 8 and input to the transmission delay generators 4 of the ultrasonic transducers. Each of the transmission delay generators 4 generates a delay to the signal transmitted to the corresponding ultrasonic transducer according to the transmission delay control signal from the delay control signal generating means 12. Preferably, the delay control signal generating means 12 generates an amplitude control signal for controlling the signal amplitude magnifying ratio of each of the transmission delay generators 4 and transmits it to the corresponding ultrasonic transducer. Each of the signal delay generators 4 has an amplifying function and can control the signal amplitude of the transmitted signal according to the amplitude control signal transmitted to it. With such an arrangement, amplitudes of the transmitted signals of each probe 1 show a distribution among the ultrasonic transducers to enable to execute an apodization process, which is well known in the technical field. As is well known, the side lobe that is produced in the ultrasonic beam transmitted from the probe 1 is suppressed to enable to efficiently irradiate the transmitted ultrasonic beam onto the target.

The transmitted pulse signal to which a predetermined time delay is given by the transmission delay generator 4 is converted into an analog signal by the D/A converter 3 and amplified by the amplifier 2 before the correspond ultrasonic transducer is driven to generate a ultrasonic wave. The ultrasonic waves generated by the ultrasonic transducers of the probe 1 are multiplexed and an ultrasonic beam that is to be converged to a predetermined transmission focusing point is transmitted into the living tissue (S25).

The transmitted ultrasonic beam is reflected by different parts of the living tissue to produce ultrasonic echoes. The delay control signal generating means 12 prepares reception delay control signals at predetermined timings by referring to the delay table and transmits them to the reception delay generators 7. Each of the reception delay generators 7 defines a delay amount according to the reception delay control signal.

The ultrasonic echoes of different parts of the living tissue are detected by the ultrasonic transducers, which by turn generates ultrasonic echo time series signals (S26). The ultrasonic echo time series signal from each of the ultrasonic transducers is amplified by the amplifier 5 thereof to an intensity level that is satisfactory relative to the noise of the apparatus and then converted into a digital signal by the A/D converter 6 before input to the reception delay generator 7.

The reception delay generator 7 of the ultrasonic transducer delays the ultrasonic echo time series signal by the delay amount defined at a predetermined timing.

The ultrasonic echo time series signal output from the reception delay generator 7 is delayed by the delay amount defined for it, which delay amount may vary from ultrasonic transducer to ultrasonic transducer in each probe and depending on the scanning method selected from various scanning methods as described above. The arrangement of delay amounts is determined as the scanning control means 11 prepares a delay table that describes the desired arrangement of delays according to the scanning method selected from various scanning methods. For this embodiment, an instance where the reception focus point is moved along the transmitted beam at a timing that corresponds to the propagation of the ultrasonic wave and the received signals of the probes are subjected to phasing addition by aperture synthesis will be described as an example.

In this instance, the ultrasonic echo time series signals output from the reception delay generators 7 are so delayed that the echo time series signals from a same point of the living tissue gets to a same time position. Therefore, the received signals can be subjected to phasing addition by aperture synthesis at the same timing. The ultrasonic echo time series signals of each probe are added by the adder 9 (S27) and subsequently all the ultrasonic echo time series signals of all the probes are added by the adder 13 (S28). The signal obtained after the phasing addition is detected by envelope detection and subsequently the image data preparing means 15 prepares image data by way of a process that is well known in the technical field. The process is summarily such that, the signals are subjected to logarithmic amplification in order to adjust the signal dynamic range to the luminance dynamic range and subsequently subjected to ultrasonic reception scanning by means a digital scan converter. Then, the signals are output to an image display apparatus or recorded in a recording means as image data.

The above-described series of processes are repeated for the number of image scanning lines to prepare a cross-sectional image of a frame or a frame image. While the transmission focus is defined for each image scanning line in the above description, a plurality of transmission focusing points can be defined for a single image scanning line. If such is the case, a set of transmission delay amounts may be prepared at the timing of switching the transmission focusing point in the delay table that is prepared by the scanning control means 11. With this arrangement, a plurality of high sound pressure points can be defined for acquiring data of a single image scanning line. Then, the ultrasonic echoes from the living tissue that correspond the image section line uniformly show a high intensity to provide an advantage of being able to prepare a highly luminance sharp image.

Figure 6:
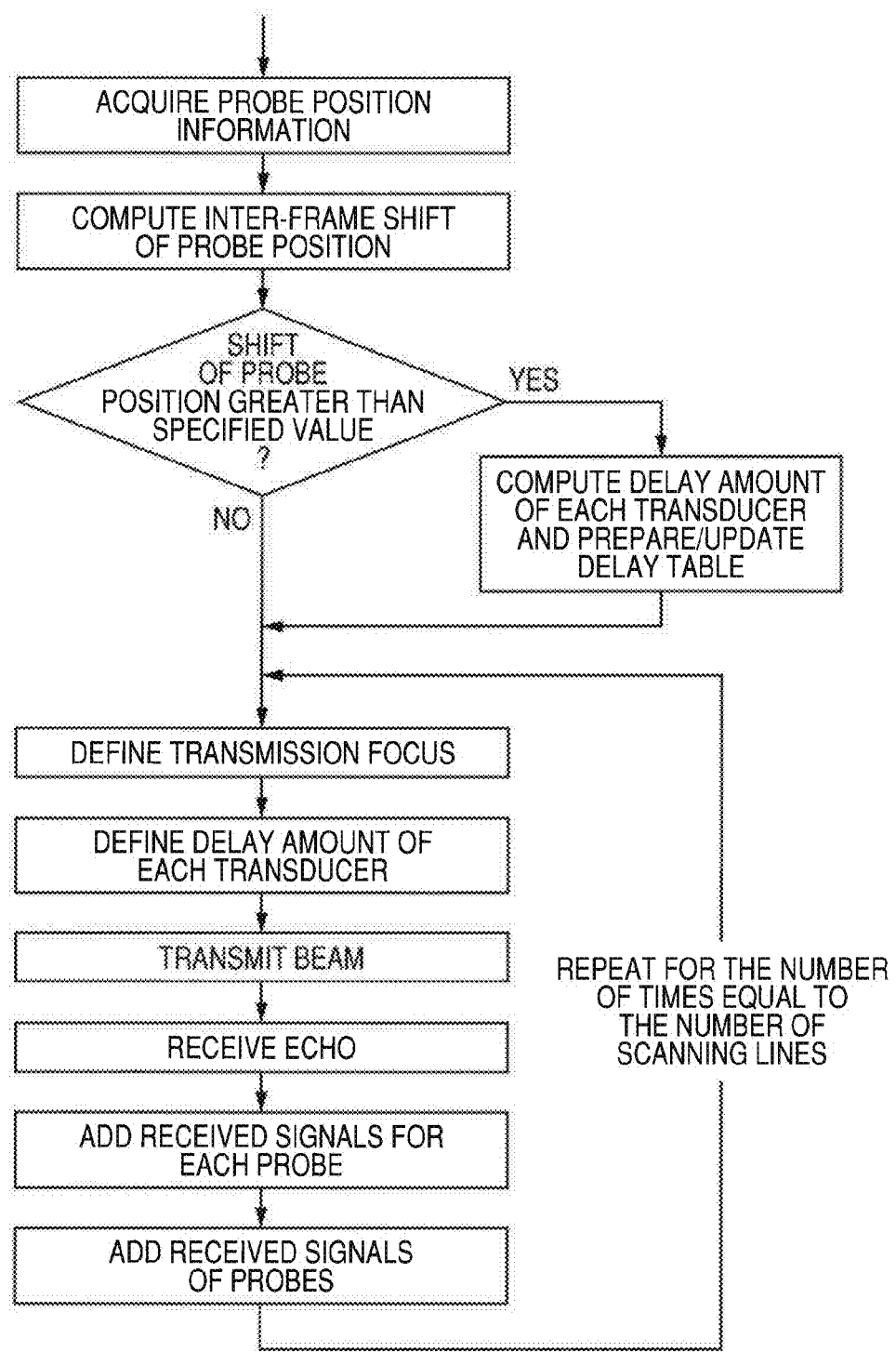
FIG. 6 is still another process flowchart illustrating the operation of the embodiment of FIG. 1.

FIG. 6 is still another process flowchart illustrating the operation of the embodiment of FIG. 1.

The process of FIG. 6 is characterized in that the position and direction detecting means acquires information each time a frame image is obtained and the delay amount computing means computes the delay amounts for a plurality of ultrasonic transducers to generate a delay control signal. As will be described hereinafter, it may be so arranged that the delay amount computing means computes again the delay amounts only when the fluctuations of the relative position and the relative angle of each of the ultrasound probes exceed a predetermined reference value among the frame images to generate a delay control signal.

Now, the process flow will be described in detail by referring to FIG. 6. This flow includes a process where the scanning control means 11 compares the position information of each of the probes acquired by the position sensor 10 with the position information of the probe used in the last frame process and it is determined if the delay table is to be updated/prepared or not according to the outcome of the comparison. Only different points from the flow of FIG. 2 will be described below. The process of FIG. 6 utilizes a memory means for storing the position information of each of the probes acquired by the position sensor 10 for each frame process and a probe position information comparing means for comparing the values of the acquired position information of each of the probes among the frames.

The apparatus has a control means for determining if the delay amounts of the transmission delay generators 4 and/or the reception delay generators 7 are to be computed and the delay table describing them is to be updated/prepared or not according to the outcome of the comparison by the probe position information comparing means. Note that FIG. 6 differs from FIG. 2 in that the apparatus of FIG. 6 has such a control means.

The memory means, the probe position information comparing means and the control means can be implemented on a processor such as a CPU by programming. The position information of each of the probes may be numerical data, the number of which may be up to 6, including the probe position $R_0$ and the orientation angle of each of the probes and the azimuth angle of the ultrasonic transducer array thereof.

Therefore, at the time of starting the frame process, the probe position information comparing means compares the position information of each of the probes acquired by the position sensor 10 with the position information of each of the probes of the last frame process stored in the memory means. The probe position information comparing means determines the difference between the position of each of the probes and the position of the probe at the last frame process and, if the difference exceeds a predefined reference value, the probe position information comparing means determines that the probe position is shifted between the two successive frame processes. Then, the apparatus proceeds to the process of computing the delay amounts for the transmission delay generators 4 and/or the reception delay generators 7 of each of the probes by means of the delay amount computing means according to the newly acquired probe position information of each of the probes and updating/preparing the delay table. If, on the other hand, the difference between the position of each of the probes according to the newly acquired position information of the probe and the position of the probe at the last frame process does not exceed the predefined reference value, the probe position information comparing means neither compute the delay amounts nor update/prepare the delay table but employs the delay table used for the last frame process for the remaining part of the process.

The numerical values stored in the memory means are replaced by the newly acquired position information of each of the probes after the comparison. Subsequently, the delay control signal generating means 12 transmits a transmission delay control signal to the transmission delay generator 4 of each of the ultrasonic transducers by referring to the delay table and the delay amount is set in the transmission delay generator 4 of the ultrasonic transducer. A process similar to the one described above by referring to FIG. 2 comes thereafter.

In the flow illustrated in FIG. 6, the position information of each of the probes acquired at the time of starting the frame process is compared with the position information of the probe used in the last frame process. Then, if the shift of the probe in terms of position and direction does not exceed a predefined value, the operation of computing the delay amounts and preparing a delay table for the frame process is omitted. Therefore, any unnecessary increase in the volume of the processing operation can be prevented from taking place when the positional shift of the probe is small, although the positional shift of the probe between two successive frame processes is appropriately accommodated. Then, as a result, the effective scanning time can be reduced to further improve the effect of minimizing the distortion of the image produced when scanning the cross section plane due to the movement of the body that is produced by heart beats or the like.

Figure 3:
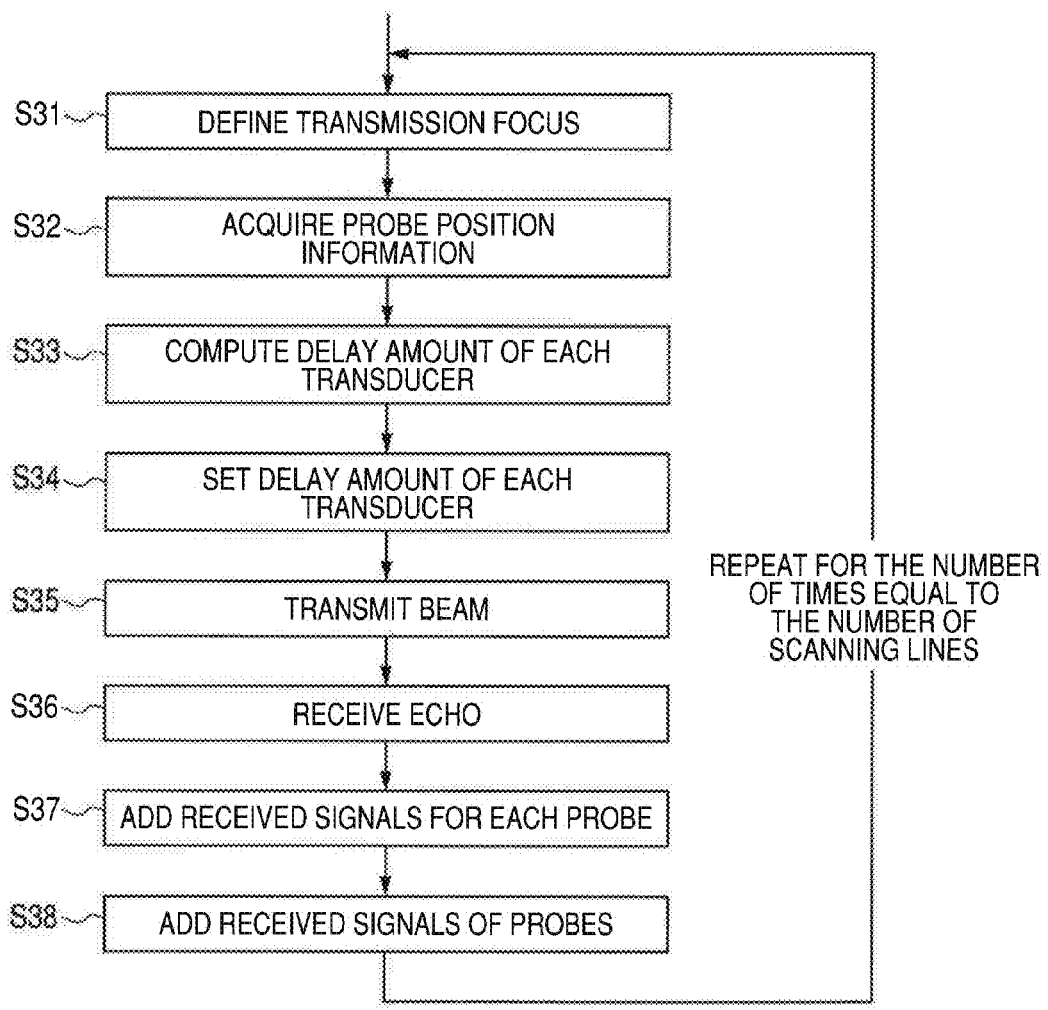
FIG. 3 is another process flowchart illustrating the operation of the embodiment of FIG. 1.

FIG. 3 is a process flowchart illustrating the operation of the embodiment of FIG. 1 that is different from the one illustrated in FIG. 2.

According to FIG. 3, the delay amounts for the plurality of ultrasonic transducers of each of the ultrasound probes are computed according to the relative position information and the relative angle information of the plurality of ultrasound probes each time the ultrasound probes respectively transmit ultrasonic beams in order to form a frame image.

The following process can be executed also for reception. The delay amounts for the plurality of ultrasonic transducers of each of the ultrasound probes are computed according to the relative position information and the relative angle information of the plurality of ultrasound probes each time the ultrasound probes respectively receive ultrasonic beams in order to form a frame image.

More specifically, information is collected from the position sensor 10 for each image scanning line of a cross section plane before each transmitting operation and each receiving operation during the scanning in a frame process. Thus, if compared with the process of FIG. 2, the time intervals of collection of probe position information is reduced because probe position information is collected from the position sensor 10 for each image scanning line.

Particularly, the position and the orientation angle of each of the probes and the azimuth angle of the ultrasonic transducer array thereof are detected immediately before each transmitting operation and each receiving operation for beam focusing. Then, the positional shift with time of each of probes can be appropriately accommodated by determining the delay amount for each of the ultrasonic transducers of each of the probes according to the information on the detection.

This arrangement provides a high degree of design freedom of implementing a plurality of probes in order to alleviate any strange feeling on the part of the target object of examination particularly in a diagnostic ultrasound apparatus and the apparatus can be formed so as to include an optical, magnetic or some other remote position sensor. Any of the probes put on the body surface can be temporally shifted with time by the heart beats or some other move on the part of the target object of examination. However, a beam scanning operation can be conducted to accommodate such a temporal shift of any of the probes by following the process flow of FIG. 3.

Now, the process flow of FIG. 3 will be described below. However, the processing steps similar to those of FIG. 2 that are described above will not be described any further.

A plurality of transmission focusing positions are defined by the scanning control means 11 according to the given scanning control signal (S31). At the same time, a plurality of reception focusing positions may be defined.

Then, the position and the orientation angle of each of the probes and the azimuth angle of the ultrasonic transducer array thereof are detected from the position sensor 10 by the delay computing means in the scanning control means 11 (S32) and the transmission delay amounts are computed (S33) and defined for the respective transducers (S34).

Additionally, delay amounts are computed and defined for reception. A plurality of reception focuses can be defined at the time of reception for a single transmission of an ultrasonic wave. If such is the case, the timings of switching the reception focuses at the time of reception and the reception delay amounts are listed in the delay amount table.

The information on the transmission delay amounts computed by the delay control signal generating means 12 is transmitted to the transmission delay generator 4 of each of the ultrasonic transducers of each of the probes as transmission delay control signal and the transmission delay amount is set in the transmission delay generator 4 (S34). At this time, the delay amount for the reception focusing position at the beginning of reception may also be transmitted to the corresponding reception delay generator 7 and set in the reception delay generator 7 in advance.

Then, the process proceeds to a transmitting operation and a focused ultrasonic beam is transmitted from each of the probes in a manner as described above by referring to FIG. 2 (S35).

Thereafter, the process proceeds to a receiving operation and a reception echo time series signal is generated from each of the ultrasonic transducers of each of the probes as described above by referring to FIG. 2 (S36) and a digitized reception echo time series signal is input to the reception delay generator 7 by way of the amplifier 5 and the A/D converter 6. The delay control signal generating means 12 transmits a reception delay control signal to the reception delay generator 7 according to the delay amount table prepared in advance at the timing of switching the reception focus. Then, it causes a delay to be produced to the echo time series signal input to each of the ultrasonic transducers of each of the probes at the timing.

Thereafter, the echo time series signals of each of the probes are subjected to phasing addition as described above by referring to FIG. 2 (S37) and all the echo time series signals are added (S38) and transmitted to the image data preparing means 15 by way of the detector 14.

The above-described series of processes are repeated for the number of image scanning lines to prepare a cross-sectional image at the image data preparing means 15.

The operation of computing the reception delay amounts and that of preparing a reception delay table may be conducted simultaneously with the operation of computing the transmission delay amounts and before a transmitting operation or during a receiving operation by the scanning control means 11 in this process. Such an arrangement provides an advantage of reducing the overall processing time without reducing the frame rate.

While delay amounts are defined for the operation of transmission and that of reception according to the position information of each of the probes from the position sensor 10 in the above description, delay amounts can be defined only for the operation of reception or transmission. If such is the case, a fixed value that corresponds to the scanning control signal can be used as the delay amount of each of the ultrasonic transducers of each of the probes in an operation of not using the position information from the position sensor 10.

Those sets of fixed delay amounts are stored in the scanning control means 11 or the delay control signal generating means 12 as a fixed delay amount table. Then, at the time of a corresponding transmitting or receiving operation, the delay amount information is sent to the delay generator 4 and/or the delay generator 7 of each of the ultrasonic transducers of each of the probes so that it may be set in the transmission delay generator 4 and/or the reception delay generator 7. Then, the operation of computing delay amounts by the scanning control means 11 can be omitted.

Still additionally, a memory means for storing the probe position information from the position sensor 10 and a probe position information comparing means may be provided so that each acquired piece of probe position information may be compared with the piece of probe position information used at the last transmitting operation and/or at the last receiving operation. Then, the delay amount computing means computes the delay amounts only when the fluctuations of the probe position information of each of the probe exceed a predetermined reference value between two successive transmitting operations and/or between two successive receiving operations so that the delay amount computing operation may be omitted when the fluctuations of the probe position is small to prevent the amount of operation of the frame process from increasing.

Figure 7:
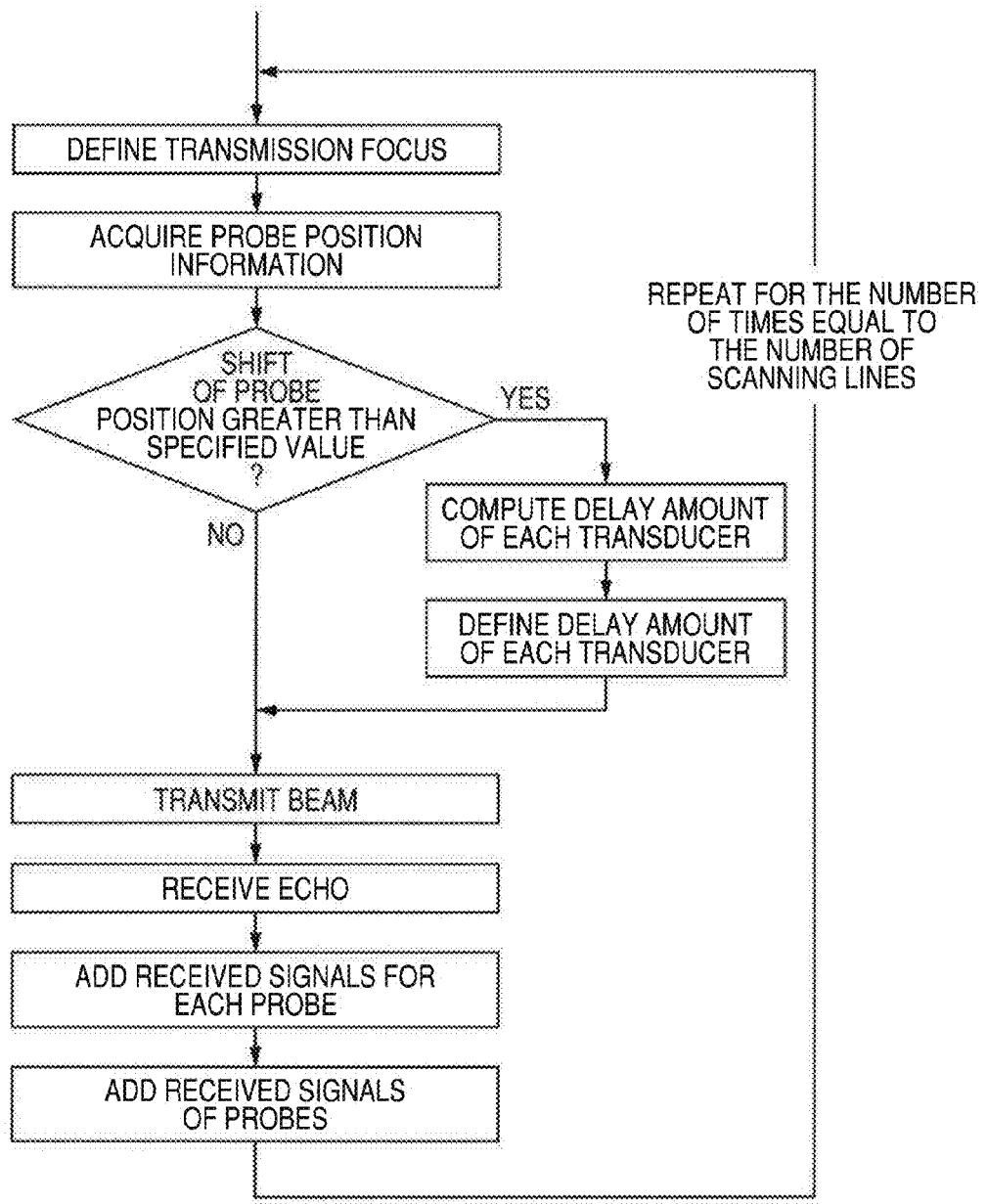
FIG. 7 is still another process flowchart illustrating the operation of the embodiment of FIG. 1.

FIG. 7 is a flowchart of such an operation of frame process.

(In the Case of Transmission)

Relative position information and relative angle information are acquired for the plurality of ultrasound probes each time the ultrasound probes transmits respective ultrasonic beams in order to form a frame image as in the flowchart of FIG. 3. However, the acquired information is compared with the information that is acquired last time and the delay amount computing means computes the delay amounts for the plurality of ultrasonic transducers only when the change in the acquired information from the last information exceeds a predetermined reference value.

(In the Case of Reception)

Relative position information and relative angle information are acquired for the plurality of ultrasound probes each time the ultrasound probes receives respective ultrasonic beams in order to form a frame image as in the flowchart of FIG. 3. However, the acquired information is compared with the information that is acquired last time and the delay amount computing means computes the delay amounts for the plurality of ultrasonic transducers only when the change in the acquired information from the last information exceeds a predetermined reference value.

The process will be described more specifically below.

At the time of starting a transmitting operation and/or a receiving operation, the probe position information comparing means compares the probe position information of each of the probes acquired by the position sensor 10 with the probe position information of the last transmitting operation and/or the last receiving operation stored in the memory means. If the difference between the position of each of the probes and the position of the probe at the last transmitting operation and/or the last receiving operation exceeds a predetermined reference value, the probe position information comparing means determines that the probe position is shifted between the two transmitting operations and/or between the two receiving operations. Then, the delay amount computing means computes the delay amount of the transmission delay generator 4 and/or the reception delay generator 7 of each of the ultrasonic transducers of each of the probes as in FIG. 3. On the other hand, if the difference between the position of each of the probes and the position of the probe at the last transmitting operation and/or the last receiving operation does not exceed a predetermined reference value, the delay amount computing means does not compute any delay amount and executes the beam transmission process and the following processes, using the delay amounts employed in the last frame process. Thereafter, the operation follows the flowchart of FIG. 3 but will not be described any further.

With the above-described arrangement, the positional shift of any of the probes is treated within a time period shorter than the one described above by referring to FIG. 6 and, when the positional shift of any probe is small, the frame process can be executed with a processing operation that is simpler than the one described above by referring to FIG. 3.

While the delay computing means is arranged in the scanning control means 11 in the above description, the delay computing means may alternatively be arranged in the delay control signal generating means 12. Particularly, when the above arrangements are realized by a digital signal processor such as a CPU, both the scanning control means 11 and the delay control signal generating means 12 can be implemented in the same processor by programming. Then, the delay computing means can be realized as processing means also by programming.

The plurality of ultrasound probes are preferably coupled to each other by a support arm coupling means as will be described in greater detail in the Example below.

EXAMPLE

Now, an example where the present invention is applied to blood flow measurement of a diagnostic ultrasound apparatus will be described below by referring to FIG. 4.

The arrangement of this example can be used for a measurement operation of determining the moving speed of tissue or the flowing speed of blood in a blood vessel at a specific position that is selected as the moving part of a specific body portion.

While an operation of measuring the blood flow rate is described below as a typical example, the following description is generally applicable to any operation of measuring the speed of a moving part of a body. The Doppler method or the color Doppler method is employed in conventional diagnostic ultrasound apparatus to measure the blood flow rate and determine the blood flow volume by using the measured blood flow rate. However, since the Doppler method and the color Doppler method are methods of detecting the phase difference of ultrasonic echo signals, they can only obtain the velocity component in the moving direction of an ultrasonic wave in principle. Conventionally, for this reason, the moving direction of the ultrasonic wave is made to agree with the flowing direction of blood, the velocity component in a direction other than the moving direction of the ultrasonic wave is estimated or the argument of the transmitted/received beam is utilized for the measurement. When the moving direction of an ultrasonic wave is made to agree with the flowing direction of blood, the measurement is subjected to restrictions. When the velocity component in a direction other than the moving direction of an ultrasonic wave is estimated, the estimation inevitably involves error. No improvement of accuracy can be expected for measurement utilizing the argument of a transmitted/received beam because beam deflection is limited when a single probe is used.

In this example, a position/direction detecting means for detecting the relative position of a plurality of ultrasound probes and the orientation of each of the ultrasound probes is employed. Then, a delay control signal generating means that generates a delay control signal for controlling the signal delay to each of the plurality of ultrasonic transducers of each of the plurality of ultrasound probes, using the information on the relative position and the orientation of the ultrasound probes obtained from the position/direction detecting means, is utilized. Large crossing angles can be selected for the beams transmitted from and received by the plurality of probes to enable to realize a highly accurate three-dimensional velocity vector measurement by controlling the delay means for delaying the transmission of each ultrasonic wave to and the reception of each ultrasonic wave from an target object of examination by means of the delay control signal.

Figure 4:
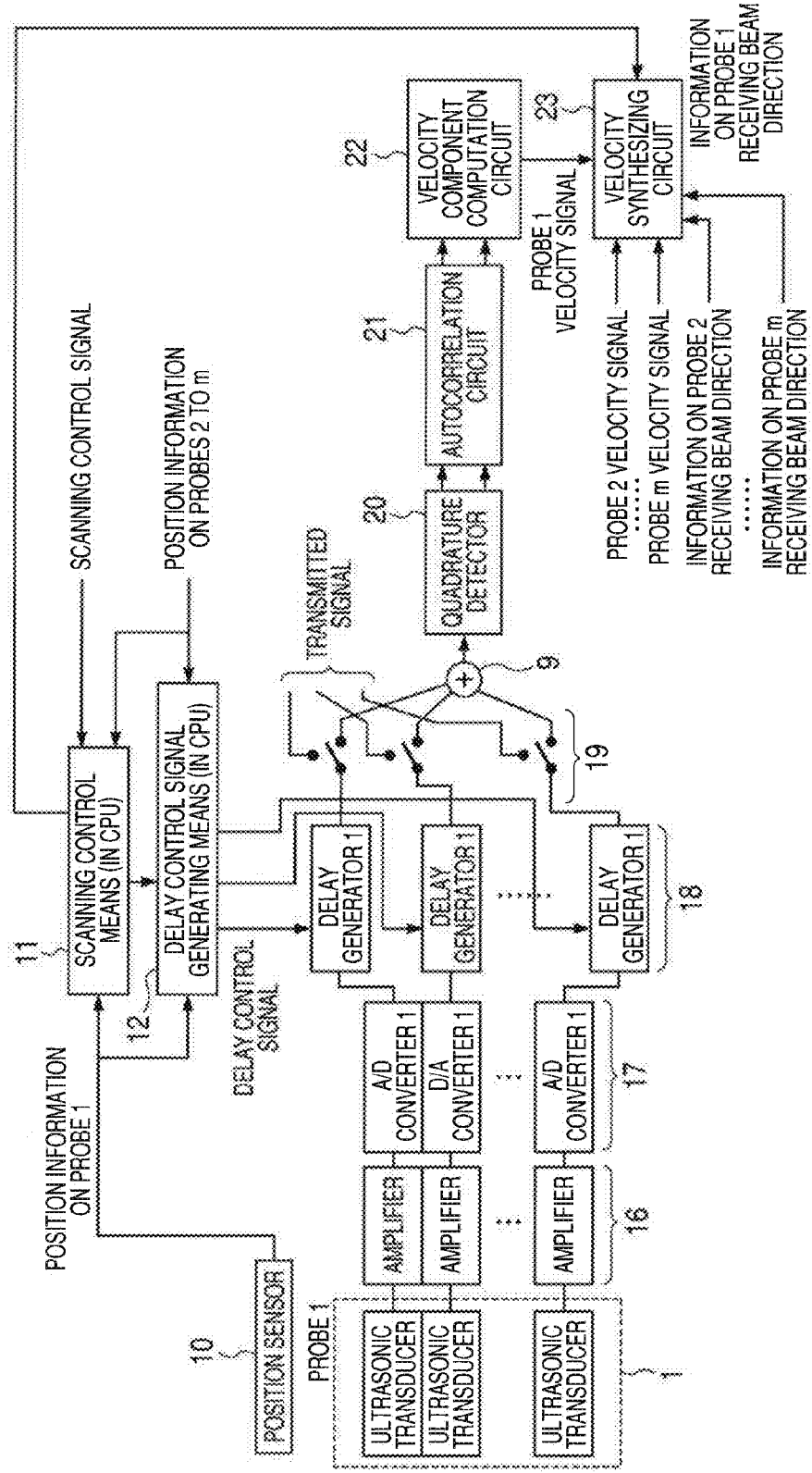
FIG. 4 is a schematic block diagram of diagnostic ultrasound apparatus employed in Example.

While only one of a plurality of probes is illustrated in FIG. 4 as in FIG. 1 for the purpose of simplicity of description, all the remaining probes have similar components. Additionally, the components same as those of FIG. 1 denoted respectively by the same reference symbols.

Transmission focusing positions are defined by the scanning control means 11 for all the points selected for measuring the speed in the body according to the given scanning control signal. At the same time, reception focusing positions are defined for all the same points. Then, the position information of the position sensor 10 on the probes including the position and the orientation angle of each of the probes and the azimuth angle of the ultrasonic transducer array thereof is acquired by the scanning control means 11. Subsequently, the transmission delay amount and the reception delay amount that correspond respectively to the transmission focusing position and the reception focusing position are computed for each of the ultrasonic transducers of each of the probes.

The delay control signal generating means 12 transmits the transmission delay amount and the reception delay amount of each of the ultrasonic transducers of each of the probes according to the transmission delay amount and the reception delay amount of the ultrasonic transducer computed by the scanning control means 11 and the transmission delay amount and the reception delay amount are set in the respective delay generators 18 of the probe.

At the same time, the scanning control means 11 computes the direction of the beam received from each of the probes according to the information on the reception focusing position and the orientation of the probe and then inputs the information on the direction of the received beam to the velocity synthesizing circuit 23.

While the amplifiers 16, the A/D-D/A converters 17 and the delay generators 18 of this example can be operated for both transmission and reception, separate ones may alternatively be provided for transmission and reception as in the case of FIG. 1. FIG. 4 denotes transmission/reception changeover switches 19 for switching transmission and reception according to the control signal from the scanning control means 11.

The quadrature detector 20, the autocorrelation circuit 21 and the velocity component computation circuit 22 are velocity detection circuits that are utilized for the color Doppler method in the technical field of diagnostic ultrasound apparatus.

The velocity synthesizing circuit 23 and the above circuits may be provided as separate digital circuits or implemented in a general purpose CPU as software just like the scanning control means 11 and the delay control signal generating means 12.

The transmission pulse signal generated by a transmission signal generating means (not illustrated) is broken down for the individual ultrasonic transducers by a separator (not illustrated) and input respectively to the delay generators 18 by way of the changeover switches 19. A transmission delay amount that corresponds to the transmission focusing position is defined in each of the delay generator 18 by the transmission delay control signal from the delay control signal generating means 12 to produce a delay to each transmission pulse signal. Subsequently, each transmission pulse signal is converted into an analog signal by a D/A converter 17 and amplified by an amplifier 16 to drive the corresponding one of the ultrasonic transducers of each of the probes so that consequently the probe transmits a focused ultrasonic beam to a predetermined transmission focusing point.

Thereafter, the changeover switch 19 is turned for reception at the time when a receiving operation starts and a reception delay control signal is input to each of the delay generators 18 from the delay control signal generating means 12 to define a reception delay amount for the delay generator 18.

Each of the ultrasonic transducers of each of the probes senses the ultrasonic echo from the target reception focusing point and generates a reception echo signal. The reception echo signal is amplified by the corresponding amplifier 16 and digitized by the corresponding A/D converter 17 before it is subjected to a delay by the corresponding delay generator 18 that corresponds to the reception focus. Thereafter, the signals of each of the probes pass through the respective transmission/reception changeover switches 19 and added by the adder 9. The addition is phasing addition because of the reception echo signals from the ultrasonic transducers of the probe agree with each other in terms of time relative to the reception focusing point because the delays produced by the delay generators 18. Then, the obtained signal is sequentially input to the quadrature detector 20, the autocorrelation circuit 21 and the velocity component computation circuit 22 to determine the velocity component of the probe in the direction of the received beam.

Generally, the plurality of probes are oriented in respective directions and the directions of the beams focused at the target object and received by different probes are different from each other. Therefore, the velocity components obtained by the velocity component computation circuits 22 are those of different directions. Thus, the velocity components obtained from ultrasonic echoes propagating in different directions from a same target point are components oriented in different directions from that point.

The velocity synthesizing circuit 23 computationally determines a three-dimensional velocity vector that is synthesized by using the information on the directions of the beams received by the probes obtained from the scanning control means 11 and the information on the velocity components obtained from the velocity component computation circuit 22 of each of the probes.

Figure 5:
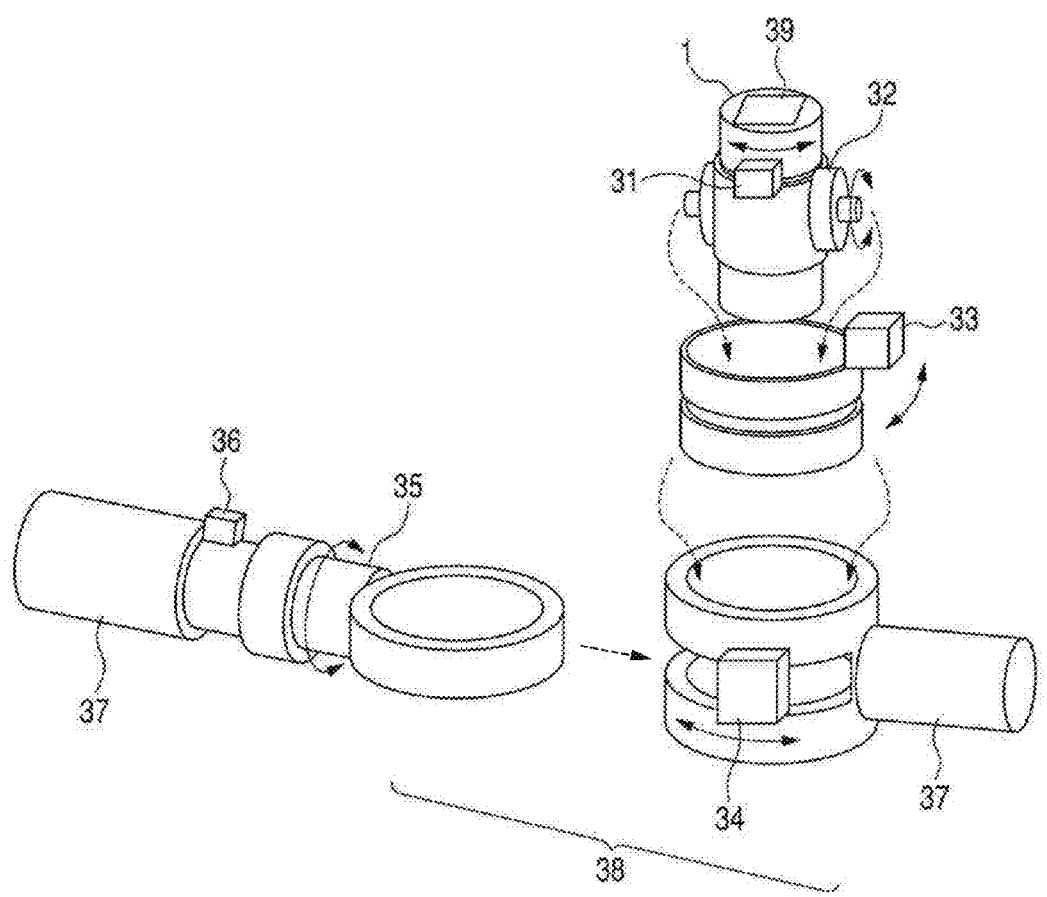
FIG. 5 is an exploded schematic perspective view of a position sensor that is used in the apparatus of Example.

FIG. 5 is an exploded schematic perspective view of a position sensor 10 that is used in this example.

In this example, the devices respectively holding the plurality of probes are equipped with respective position sensors.

Each of the probe holding devices includes a support arm 37 and a probe holding section 38. Each of the position sensors includes a linear sensor 36 and a rotary encoder 35 arranged at the corresponding support arm 37 and four rotary encoders 31, 32, 33 and 34 arranged at the corresponding probe holding section 38. The support arm 37 can be freely engaged in position and disengaged from the position and its length can be made to change and measured by means of the linear sensor 36. Any two support arms 37 can be connected to each other by way of a probe holding section 38 and the angle between the support arms can be changed and measured by the rotary encoder 34. The angle of the holding arm 37 in the axis direction can be measured by the rotary encoder 35. The orientation of each probe can be shifted by means of the probe holding section 38 and its elevation angle and azimuth angle can be measured respectively by the rotary encoders 32 and 33. The azimuth angle of the ultrasonic transducer array 39 on the probe can be measured by the rotary encoder 31.

The relative position of the probe and another probe coupled to the former probe can be detected by means of the linear sensor 36 and the rotary encoders 34 and 35 and the orientation of the probe can be detected by the rotary encoders 32 and 33, while the relative azimuth angle of the ultrasonic transducer array 39 can be detected by the rotary encoder 31.

The probe position information from the position sensor 10 can be computationally determined by means of the above-described arrangement.

The diagnostic ultrasound apparatus of this example can be formed so as to include support arms connected to the respective ultrasound probes and having a variable length and a length detection means for detecting the length of each of the support arms. The orientation angles of ultrasound probes coupled by a support arm can be measured. Support arms can be coupled directly or by way of a support arm coupling means. All the ultrasound probes can be coupled to each other and one or more than one angle detection means can be provided so as to make it or each of them, whichever appropriate, detect the angle between two support arms or between a support arm and a support arm coupling means. Then, information relating to the relative positions and the relative orientations of the plurality of ultrasound probes can be obtained from the outputs of the length detection means and the angle detection means.

A diagnostic ultrasound apparatus according to the present invention can be arranged as a single unit relative to a target object of examination by supporting a plurality of probes collectively by means of a support device and arranging a position sensor thereon and the position and the orientation of each of the probes can be freely selected so that the plurality of probes can be arranged in a simple manner for diagnosis.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2008-138055 filed May 27, 2008 and 2009-097225 filed Apr. 13, 2009, which are hereby incorporated by reference herein in their entirety.

What is claimed is:

1. A diagnostic ultrasound apparatus for transmitting ultrasonic waves to a target object, receiving ultrasonic waves reflected from the target object and generating image data relating to the target object based on acquired echo signals, said apparatus comprising:
a plurality of ultrasound probes, each being formed to include a plurality of ultrasonic transducers;
delay circuitry deployed to electronically delay the timing of transmission of ultrasonic waves from said ultrasonic transducers; and
position-and-orientation sensors provided respectively in said plurality of ultrasound probes to detect information as to relative position and relative angle with respect to each other of said plurality of ultrasound probes,
wherein said delay circuitry controls the timing of transmission of ultrasonic waves from respective ones of said ultrasonic transducers according to the information as to relative position and relative angle with respect to each other of said plurality of ultrasound probes that was acquired from said position-and-orientation sensors so that ultrasonic waves transmitted from said plurality of ultrasound probes are in phase and combined with each other in a crossing region of the transmitted waves.

2. The apparatus according to claim 1, wherein ultrasonic beams transmitted from said ultrasound probes are subjected to beam scanning so as to change the respective directions of transmission thereof, and said apparatus further comprising:
a central processing unit and memory, said central processing unit and memory cooperating to function as:
a delay amount computing unit for determining a delay amount for each of said ultrasonic transducers according to relative position information and relative angle information of said plurality of ultrasound probes at the time of starting the beam scanning or during the beam scanning.

3. The apparatus according to claim 2, further comprising a delay amount table, wherein results of computation by said delay amount computing units are written to said delay amount table before said ultrasound probes start the beam scanning and said ultrasonic transducers are controlled for signal delays during the beam scanning according to said delay amount table.

4. The apparatus according to claim 2, wherein said position-and-orientation sensors acquire relative position information and relative angle information of said ultrasound probes and said delay amount computing unit computes delay amounts for said ultrasonic transducers and generates a delay control signal each time said apparatus acquires a frame image.

5. The apparatus according to claim 4, wherein said delay amount computing unit computes the delay amounts for said ultrasonic transducers again to generate a delay control signal only when the difference in the relative position information and the relative angle information of said ultrasound probes among the acquired frame images exceeds a reference value.

6. The apparatus according to claim 2, wherein said delay amount computing unit computes delay amounts for said ultrasonic transducers according to relative position information and relative angle information of said ultrasound probes each time said ultrasound probes transmit ultrasonic beams in order to form a frame image.

7. The apparatus according to claim 6, wherein said apparatus acquires relative position information and relative angle information of said ultrasound probes each time said ultrasound probes transmit respective ultrasonic beams to form a frame image and compares the acquired information with the last information and said delay amount computing unit computes the delay amounts for said ultrasonic transducers again only when the difference in the relative position information and the relative angle information of said ultrasound probes exceeds a reference value.

8. The apparatus according to claim 2, wherein ultrasonic beams transmitted from said ultrasound probes are subjected to focusing by said delay circuitry.

9. The apparatus according to claim 1, wherein said plurality of ultrasound probes are coupled to each other by a support arm coupling unit.

10. A diagnostic ultrasound apparatus for transmitting ultrasonic waves to a target object, receiving ultrasonic waves reflected from the target object and generating image data relating to the target object based on acquired echo signals, said apparatus comprising:
a plurality of ultrasound probes, each being formed to include a plurality of ultrasonic transducers;
delay circuitry deployed to electronically delay reception signals from the plurality of ultrasound probes; and
position-and-orientation sensors arranged respectively in said plurality of ultrasound probes to detect information as to relative position and relative angle with respect to each other of said plurality of ultrasound probes, wherein said delay circuitry controls electronically delaying the reception signals according to the information as to relative position and relative angle with respect to each other of said plurality of ultrasound probes that was acquired from said position-and-orientation sensors so that reception signals, corresponding to ultrasonic waves from a same point of the target object, from said plurality of ultrasound probes are in phase with each other.

11. The apparatus according to claim 10, wherein ultrasonic beams received by said ultrasound probes are subjected to beam scanning so as to change the respective directions of reception thereof, and said apparatus further comprising:
a central processing unit and memory, said central processing unit and memory cooperating to function as:
a delay amount computing unit for determining a delay amount for each of said ultrasonic transducers according to relative position information and relative angle information of said plurality of ultrasound probes at the time of starting the beam scanning or during the beam scanning.

12. The apparatus according to claim 11, wherein ultrasonic beams reflected from the target object of examination are subjected to focusing by said delay circuitry.

13. The apparatus according to claim 11, wherein said delay amount computing unit computes delay amounts for said ultrasonic transducers according to relative position information and relative angle information of said ultrasound probes each time said ultrasound probes receive respective ultrasonic beams to form a frame image.

14. The apparatus according to claim 13, wherein said apparatus acquires relative position information and relative angle information of said ultrasound probes each time said ultrasound probes receive respective ultrasonic beams to form a frame image and compares the acquired information with the last information and said delay amount computing unit computes the delay amounts for said ultrasonic transducers again only when the difference in the relative position information and the relative angle information of said ultrasound probes exceeds a reference value.

* * * * *